US009896360B2

(12) United States Patent
Garusi et al.

(10) Patent No.: US 9,896,360 B2
(45) Date of Patent: Feb. 20, 2018

(54) HOT SANITARY WATER SYSTEM AND METHOD FOR DISINFECTION OF HOT WATER

(71) Applicant: Sanipur S.r.l., Flero, Brescia (IT)

(72) Inventors: Gianfranco Garusi, Flero (IT); Francesco Garusi, Flero (IT)

(73) Assignee: Sanipur S.r.l., Flero (IT)

(*) Notice: Subject to any disclaimer, the term of this patent is extended or adjusted under 35 U.S.C. 154(b) by 593 days.

(21) Appl. No.: 14/576,484

(22) Filed: Dec. 19, 2014

(65) Prior Publication Data

US 2015/0329391 A1    Nov. 19, 2015

(30) Foreign Application Priority Data

May 16, 2014    (IT) ............................... MI2014A0898

(51) Int. Cl.
*C02F 1/76*    (2006.01)
*A61L 2/18*    (2006.01)
(Continued)

(52) U.S. Cl.
CPC ............... *C02F 1/76* (2013.01); *A01N 59/00* (2013.01); *A61L 2/18* (2013.01); *C02F 2103/42* (2013.01);
(Continued)

(58) Field of Classification Search
CPC .......... C02F 1/50; C02F 1/76; C02F 2103/42; C02F 2209/005; C02F 2209/04;
(Continued)

(56) References Cited

U.S. PATENT DOCUMENTS 4,614,595 A * 9/1986 Azzarella ................. C02F 1/76
                                                      210/754
6,315,950 B1 * 11/2001 Harp ..................... G01N 33/182
                                                      422/28
(Continued)

FOREIGN PATENT DOCUMENTS

EP    2 218 687 A1    8/2010
GB    2 368 838 A     5/2002
(Continued)

OTHER PUBLICATIONS

English language machine translation of JP 2008-264678. Retrieved from https://worldwide.espacenet.com on Jul. 26, 2017.*
(Continued)

*Primary Examiner* — Jason M Greene
(74) *Attorney, Agent, or Firm* — Blank Rome LLP (57) ABSTRACT

A sanitary warm water system comprises an annular water duct, a pump, a heater, withdrawing ducts connected to the annular duct and a supply duct, a monochloramine generator which synthesizes and adds monochloramine to the warm water in the annular duct at a disinfection point, an ammonium ion abatement device which adds chlorine or hypochlorites to the warm water in the annular duct, an ammonium detector which detects the concentration of ammonium ions in the warm water and a control system which activates the monochloramine generator and activates the ammonium ion abatement device and controls the addition of chlorine or hypochlorite as a function of the ammonium concentration signals, independently of the activation of the monochloramine generator.

12 Claims, 4 Drawing Sheets

(51) Int. Cl.
  *A01N 59/00* (2006.01)
  *C02F 103/42* (2006.01)
(52) U.S. Cl.
  CPC .... *C02F 2209/005* (2013.01); *C02F 2209/04* (2013.01); *C02F 2209/14* (2013.01); *C02F 2209/29* (2013.01); *C02F 2303/04* (2013.01); *C02F 2305/02* (2013.01); *C02F 2307/14* (2013.01)
(58) Field of Classification Search
  CPC .............. C02F 2209/14; C02F 2209/29; C02F 2305/02; C02F 2307/14; A01N 59/00; A61L 2/18; A47K 3/00
  USPC .................................................. 210/739, 754
  See application file for complete search history.

(56) References Cited

U.S. PATENT DOCUMENTS

| | | | |
|---|---|---|---|
| 2002/0162802 A1* | 11/2002 | Simmons | C02F 1/686 210/739 |
| 2003/0029811 A1* | 2/2003 | Russell | C02F 1/76 210/749 |
| 2005/0211643 A1* | 9/2005 | Phillips | C02F 1/76 210/753 |
| 2006/0124558 A1 | 6/2006 | Kouame | |
| 2009/0134096 A1 | 5/2009 | Giti et al. | |
| 2009/0173697 A1* | 7/2009 | Axtell | C02F 1/76 210/744 |
| 2010/0206815 A1* | 8/2010 | Garusi | C02F 1/76 210/739 |
| 2012/0021062 A1* | 1/2012 | Gupta | C02F 1/50 424/600 |
| 2012/0074070 A1* | 3/2012 | Sichel | C02F 1/32 210/745 |
| 2015/0203388 A1* | 7/2015 | Gotthardt | C02F 1/50 210/739 |
| 2015/0367315 A1* | 12/2015 | Barak | C02F 1/76 423/659 |

FOREIGN PATENT DOCUMENTS

| | | |
|---|---|---|
| JP | 10-28981 A | 2/1998 |
| JP | 2008-264678 A | 11/2008 |
| WO | WO 2004/007378 A2 | 1/2004 |

OTHER PUBLICATIONS

L. J. Swango et al., "Inactivation of Legionella Pneumophila by Hypochlorite and an Organic Chloramine." Applied and Environmental Microbiology, vol. 53, No. 12, pp. 2983-2986, Dec. 1987.

* cited by examiner

HOT SANITARY WATER SYSTEM AND METHOD FOR DISINFECTION OF HOT WATER

BACKGROUND OF THE INVENTION

1. Field of the Invention

The present invention relates to a method and system for the disinfection of sanitary warm water.

2. Description of the Related Art

The warm water used for hygienic and sanitary, but also for technical, industrial and zoo-technical purposes may harbor microorganisms dangerous to human health, such as *Legionella* present in warm water and responsible for a bacterial infection, Legionellosis, which can strike humans with a high mortality rate, especially in a hospital setting.

In water at moderate temperatures, not exceeding 30° C., *Legionella* can be found naturally in very low concentrations, considered non-critical from a health point of view.

In warm water instead, at temperatures up to about 65° C., *Legionella* proliferates significantly, reaching concentrations dangerous for human health.

As a result, the warm water for sanitary and technical use, for example in the range from 45° C. to 50° C., in bathrooms, showers, cooling towers, etc. can be a dangerous source of infection by *Legionella* bacteria.

The proliferation of *Legionella* bacteria is particularly critical in constant environmental conditions, such as in hospitals, hotels, ships, swimming pools and the like where the water is kept hot in a constant range of temperature and often stagnates in piping.

There are several ways to combat *Legionella* and clean contaminated plumbing.

One method of disinfection is the increase in water temperature, hyperthermia or thermal shock at 70° C. . . . 80° C., for a few minutes a day so as to eliminate the bacterial colonies. The application of thermal shock is however limited since hydraulic systems operating discontinuously cannot ensure the temperature limit is reached in remote points, such as in the terminal withdrawal points of the water, where the maximum temperature reached is often lower than 60° C.

Among the chemical methods, the chlorination of water is known both in the cleaning of plants, and in preserving their salubriousness. However, chlorination involves the formation of chlorinated organic by-products of proven toxicity (THM—trihalomethane chlorinates).

The use of chlorine and hypochlorites is also not recommended because the biofilm is not significantly attacked and destroyed.

More widespread in the purification of drinking water is the use of chlorine dioxide which, being oxidant, prevents the formation of organic chlorinates. However, chlorine dioxide does not have selective properties and thus also attacks the pipes, especially the latest generation plastic pipes of the plumbing system.

According to recent scientific studies and applications in the field, the use of monochloramine ($NH_2Cl$) appears effective in treating drinking water against the proliferation of *Legionella* and in the preservation of the salubriousness of hydraulic systems, without however attacking the plastic pipes.

Studies and applications in the field basically indicate two main ways of introducing monochloramine into the water.

The first way is to synthesize monochloramine in a suitable reactor which provides for the dosing of the reagents, for example by means of the reaction $NH_3\ Cl_2 \rightarrow NH_2Cl + HCl$, and to introduce the monochloramine previously synthesized, for example in aqueous solution, into the warm water to be disinfected. The second way is to produce the monochloramine directly in the warm water to be disinfected, adding the reagents, chlorine or hypochlorite and ammonia or ammonium salts, to the warm water. Both methods appear feasible, but have some drawbacks in the control of the concentration of monochloramine and its decomposition by-products, especially the ammonium ions ($NH_4^+$).

In warm water recirculation systems such as in hospitals and swimming pools, only a part of the water with monochloramine already added is withdrawn, while the remaining portion remains in circulation in the system and is cyclically re-heated, facilitating the thermal decomposition of the monochloramine in the system and requiring the addition of fresh water with monochloramine not yet added to it. This exacerbates the problem of variations in the concentration of monochloramine and the excessive accumulation of decomposition by-products, in particular ammonium ions, in the recirculated warm water.

A further requirement not yet completely satisfied consists in the practical application of the principles of disinfection by monochloramine by means of technically robust, economical and versatile solutions applicable to existing water distribution plants.

SUMMARY OF THE INVENTION

The purpose of the present invention is therefore to propose a method and system for the disinfection of warm water by means of monochloramine, having characteristics such as to overcome at least some of the drawbacks mentioned with reference to the prior art.

These and other purposes are achieved by a sanitary warm water recirculation system (1) with:

a water annular duct (2), a pump (3) connected with the annular duct (2) in a pumping point (4) to circulate water in the annular duct (2), heating means (5) connected with the annular duct (2) in a heating point (6) and configured to heat the water during the passage thereof through the heating point (6), one or more withdrawing ducts (7) connected with the annular duct (2) at respective withdrawing points (8), a supplying duct (9) connected with the annular duct (2) in a supplying point (10), wherein the sanitary water system further comprises a disinfection system (11) having:

an electronic control system (12), a monochloramine generator (13) in signal connection with the control system (12) and connected with the annular duct (2) in a disinfectant insertion point (14), wherein the generator (13) is configured to synthesize monochloramine and to add the synthesized monochloramine to the warm water in the disinfectant insertion point (14), a ammonium ion abatement device (15) in signal connection with the control system (12) and connected with the annular duct (2) in an abatement point (16), wherein the abatement device (15) is configured to add chlorine or hypochlorites to the water at the abatement point (16), ammonium detecting means (17) in signal connection with the control system (12) and connected with the annular duct (2) at an ammonium detecting point (18), the ammonium detecting means (17) being configured to detect a quantity representative of the ammonium ion concentration in the warm water at the ammonium detecting point (18), and to transmit a corresponding ammonium concentration signal to the control system (12), wherein the control system (12):
    activates the monochloramine generator (13) and controls the monochloramine synthesis and addition, and
    activates the ammonium ion abatement device (15) and controls the chlorine or hypochlorite addition as a function of the ammonium concentration signals, independently from the monochloramine generator (13) activation.

These and other purposes are also achieved by a method for the disinfection of a warm water recirculation system (1) with:
    a water annular duct (2),
    a pump (3) connected with the annular duct (2) in a pumping point (4) to circulate water in the annular duct (2),
    heating means (5) connected with the annular duct (2) in a heating point (6) and configured to heat water during the passage thereof through the heating point (6),
    one or more withdrawing ducts (7) connected with the annular duct (2) at respective withdrawing points (8),
    a supplying duct (9) connected with the annular duct (2) in a supplying point (10),
    wherein said method comprises the steps of:
    synthesizing monochloramine in a monochloramine generator (13) externally to the warm water recirculation system (1) and adding the previously synthesized monochloramine to the warm water at a disinfectant insertion point (14) of the annular duct (2),
    adding chlorine or hypochlorites to the warm water at a abatement point (16) of the annular duct (2),
    detecting an ammonium ion concentration in the warm water at an ammonium detecting point (18) of the annular duct (2),
    metering the chlorine or hypochlorite addition at the abatement point (16) as a function of the detected ammonium ion concentration and independently from the monochloramine generator (13) activation.

BRIEF DESCRIPTION OF THE DRAWINGS

For a better understanding of the invention and its advantages, some of its embodiments will be described below by way of non-limiting examples, with reference to the appended drawings, wherein.

DETAILED DESCRIPTION OF THE PREFERRED EMBODIMENTS

According to the invention, the method and disinfection system is applicable to warm water recirculating systems 1 comprising:

an annular water duct 2,
a pump 3 connected to the annular duct 2 at a pumping point 4 to make the water circulate in the annular duct 2,
heating means 5, such as an electric or gas boiler, connected to the annular duct 2 in a heating point 6 and configured to heat water upon its transit through the heating point 6,
one or more withdrawal ducts 7 connected to the annular duct 2 at respective withdrawal points 8,
a supply duct 9 connected to the annular duct 2 at a supply point 10,
optionally, a water tank connected to the annular duct 2.

In normal use of the recirculation system 1, the pump 3 makes the water circulate in the annular duct 2 through the heating means 5 which heat it to keep the water temperature within a predetermined range. The warm water is made available to users through the withdrawal ducts 7 and the volume of water withdrawn through the withdrawal ducts 7 is replenished by means of the supply pipe 9 to keep the total volume and the water pressure in the recirculation system within a predetermined range and suitable for correct operation of the recirculation system 1.

According to one aspect of the invention, the disinfection system 11 comprises:
    an electronic control system 12, such as a single central controller or two or more independent controllers,
    a monochloramine generator 13 in signal connection with the control system 12 and connected to the annular duct 2 at a disinfectant insertion point 14, wherein the generator 13 is configured to synthesize monochloramine and to add the synthesized monochloramine to the water at the disinfectant insertion point 14 of the annular duct 2,
    an ammonium ion abatement device 15 in signal connection with the control system 12 and connected to the annular duct 2 at an abatement point 16, wherein the abatement device 15 is configured to add chlorine or hypochlorites to the water at the abatement point 16 of the annular duct 2,
    ammonium detection means 17 in signal connection with the control system 12 and connected to the annular duct 2 at an ammonium detection point 18, the ammonium detection means 17 being configured to detect a quantity representative of the ammonium ion concentration in the water at the ammonium detection point 18 of the annular duct 2 and to transmit a corresponding ammonium concentration signal to the control system 12,
    wherein the control system 12 is configured to:
    activate the monochloramine generator 13 and control the synthesis and addition of monochloramine and
    activate the ammonium ion abatement device 15 and control the addition of chlorine or hypochlorites as a function of the ammonium concentration signals, independently of the activation of the monochloramine generator 13.

This makes it possible on the one hand to synthesise monochloramine in optimum synthesis conditions inside the monochloramine generator 13 and on the other hand, to independently control the concentration of decomposition by-products of the monochloramine, by an addition of chlorine or hypochlorites in amounts and times independent of the operation of the monochloramine generator 13.

A further advantageous effect of the independent activation of the addition of hypochlorites to the warm water is that of being able to use an excess of hypochlorites as additional disinfectant.

Figure 5:
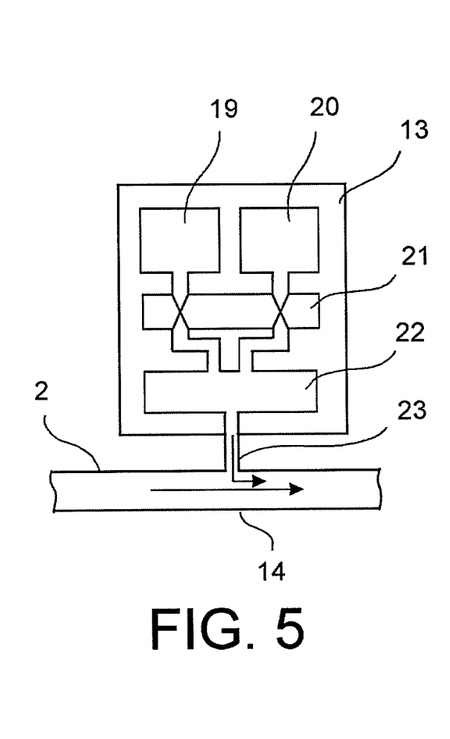
FIG. 5 shows a monochloramine generator of the disinfection system according to an embodiment.

In one embodiment (FIG. 5), the monochloramine generator 13 synthesizes the monochloramine externally to the warm water of the recirculation system 1 and supplies the previously synthesized monochloramine to the annular duct 2. To such purpose, the generator 13 may comprise a first recipient 19 containing chlorine or hypochlorites and a second recipient 20 containing ammonia or ammonium salts, connected by means of a metering system 21 to a reaction chamber 22 where the synthesizing of monochloramine takes place, and a single duct 23 which connects the reaction chamber 22 to the disinfectant insertion point 14 of the annular duct 2.

Figure 6:
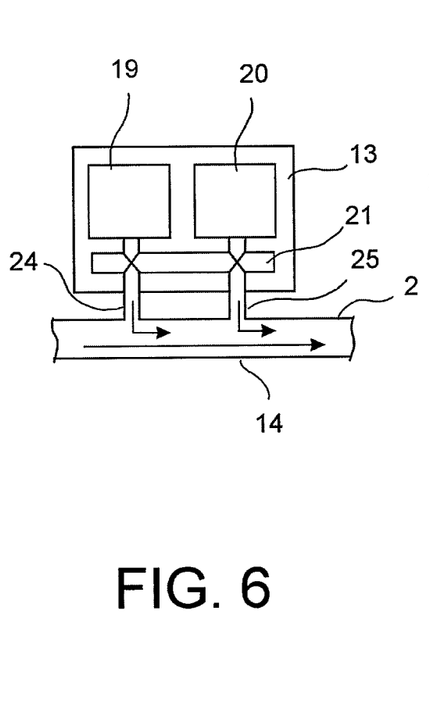
FIG. 6 shows a monochloramine generator of the disinfection system according to a further embodiment.
Figure 7:
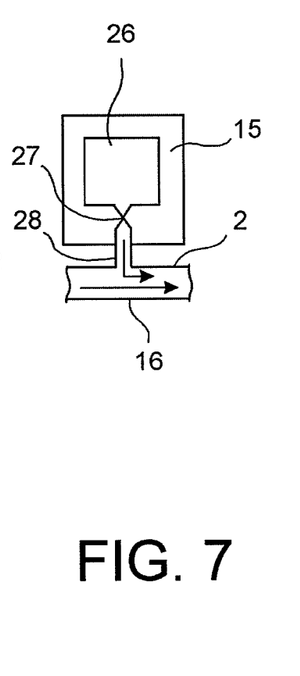
FIG. 7 shows a chlorine or hypochlorite meter of the disinfection system according to one embodiment.

In an alternative embodiment (FIG. 6), the monochloramine generator 13 synthesises the monochloramine directly in the warm water of the recirculation system. To such purpose, the generator 13 may comprise a first recipient 19 of chlorine or hypochlorites and a second recipient 20 of ammonia or ammonium salts, connected by means of a metering system 21 to two separate ducts 24, 25 in turn connected to the disinfectant insertion point 14 of the annular duct 2, so as to introduce the two reagents separately into the warm water inside the annular duct 2 and make them react after the introduction thereof into the warm water.

The ammonium ion abatement device 15 comprises a chlorine or hypochlorite recipient 26 connected via a metering device 27 and a dispensing duct 28 to the abatement point 16 of the annular duct 2.

In one embodiment, the abatement point 16 is distant from the disinfectant insertion point 14. This enables the addition of chlorine or hypochlorites in the regions of the annular duct 2 or its ramifications which show a higher concentration of ammonium ions, regardless of the position of the monochloramine generator 13.

Figure 1:
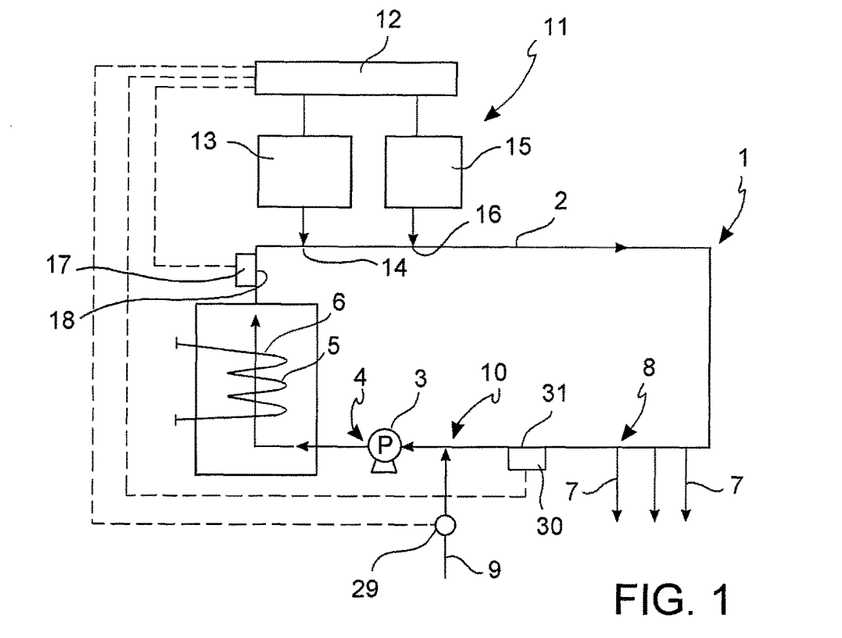
FIG. 1 is a schematic representation of the disinfection system applied to a warm water circulation system according to one embodiment of the invention.
Figure 2:
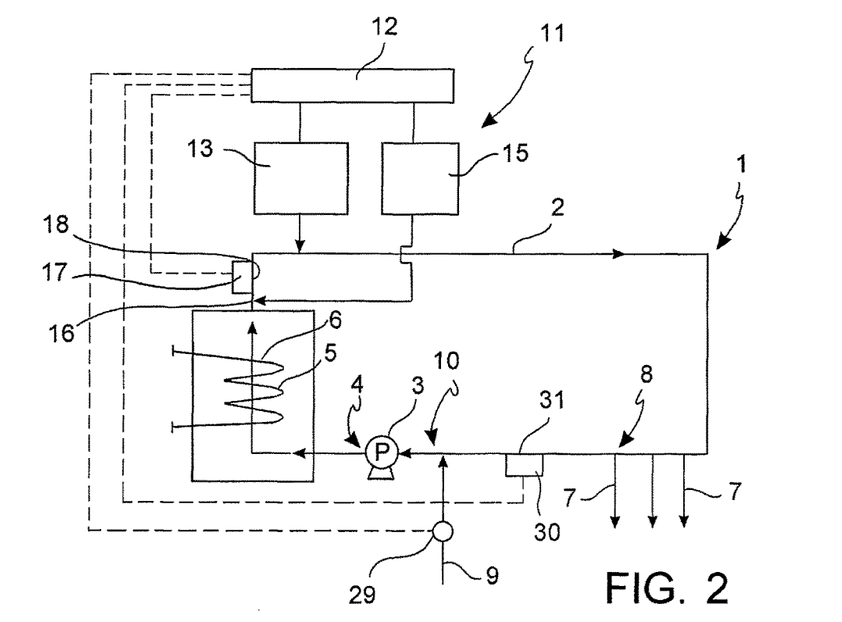
FIGS. 2 to 4 illustrate further embodiments of the disinfection system.
Figure 3:
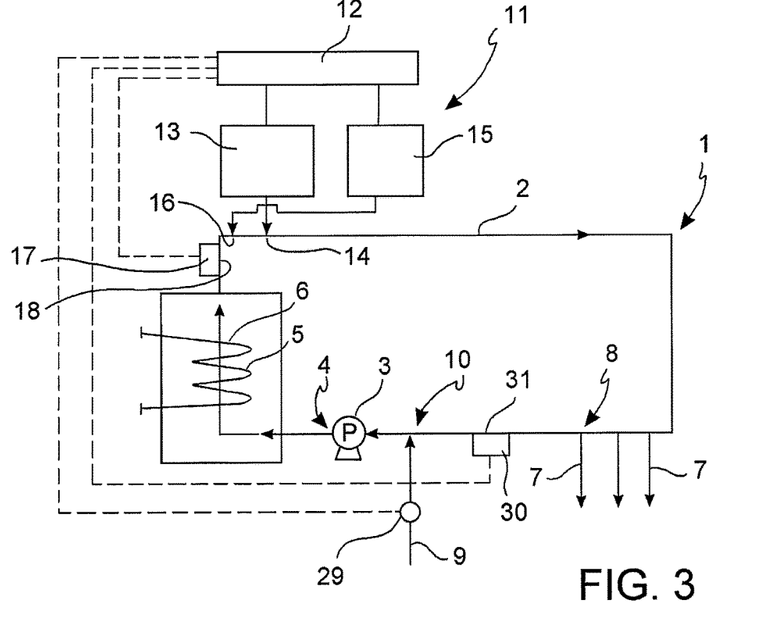

In one embodiment (FIGS. 1, 2, 3) the disinfectant insertion 14 and abatement 16 points are both downstream of the heating means 5 and upstream of the withdrawal points 8, seen in the direction of the circulation of the water. This makes it possible to compensate a lowering of the concentration of monochloramine and absorb the free ammonium ions after a phase of more intense thermal decomposition of the monochloramine in the heating point 6 and before the withdrawal and use of the warm water.

In another embodiment (FIG. 1), the abatement point 16 is downstream of the disinfectant insertion point 14 seen in the direction of the circulation of the water, and the monochloramine generator 13 synthesises the monochloramine with a slight excess of chlorine.

This permits a basic control of the levels of free ammonium ions as a function of constant characteristics of the recirculation system of warm water 1 directly via the monochloramine generator 13 and, in the event of exceptional and unexpected variations in the concentration of ammonium ions, the further operation of the ammonium ion abatement device.

In a further embodiment (FIGS. 2, 3), the abatement point 16 is upstream of the disinfectant insertion point 14, seen in the direction of the circulation of the water. Such configuration permits the reduction of the decomposition by-products of monochloramine before the addition of fresh monochloramine in the annular duct 2.

In this embodiment, the ammonium detection point 18 is advantageously downstream of the heating point 6 and upstream of the abatement point 16 (FIG. 3) to prevent alterations of the ammonium concentration signal due to the addition of chlorine or hypochlorites just before the ammonium detection point 18.

The placing of the ammonium detection point 18 downstream of the abatement point 16 (FIG. 2) is also provided for to partially offset the fall in the monochloramine concentration in the heating point 6 before the ammonium detection point 18 and to prevent bacteria from lurking precisely in the ammonium detection point 18.

Figure 4:
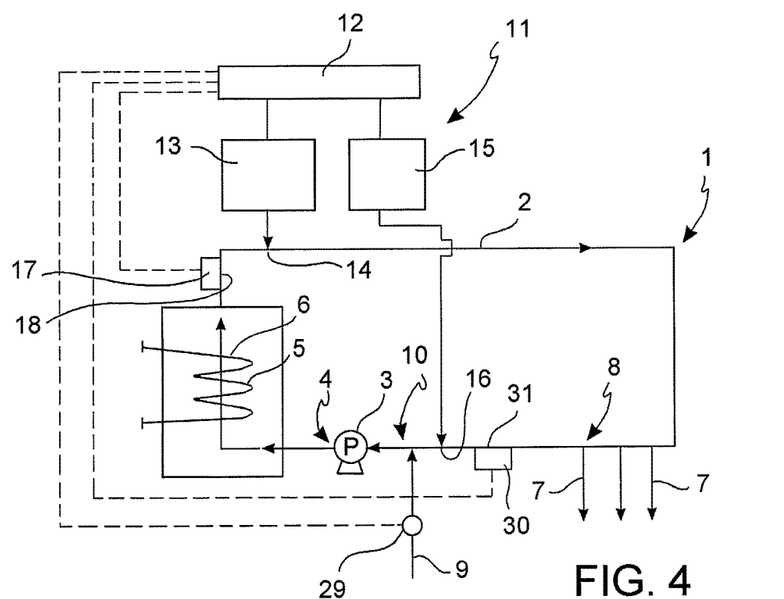

In yet another embodiment (FIG. 4) the abatement point 16 is downstream of the withdrawal points 8 and upstream of the heating point 6 seen in the water flow direction in the annular duct (2).

In one embodiment (FIGS. 1-4) the disinfection system 11 further comprises a flow detector 29 in signal connection with the control system 12 and connected with the supply duct 9, the flow detector 29 being configured to detect a quantity representative of the water volume supplied at the supply point 10 of the annular duct 2 and to transmit a corresponding volume signal to the control system 12. The control system 12 is configured to activate the monochloramine generator 13 and control the synthesis and addition of monochloramine as a function of the volume signal and, possibly, as a function of time, for example on the basis of known characteristics of monochloramine decomposition.

In addition or as an alternative (FIGS. 1-4), the disinfection system 11 may comprise monochloramine detection means 30 in signal connection with the control system 12 and connected with the annular duct 2 at a monochloramine detection point 31, the monochloramine detection means 30 being configured to detect a quantity representative of the monochloramine concentration in the water at the monochloramine detection point 31 of the annular duct 2 and to transmit a corresponding monochloramine concentration signal to the control system 12. In this case the control system 12 is configured to actuate the monochloramine generator 13 and to control the synthesis and addition of monochloramine (also) as a function of the monochloramine concentration signal.

The monochloramine detection point 31 may be in the sections of annular duct 2 previously indicated for the positioning of the ammonium detector 17 (and not repeated here for brevity), or, alternatively, downstream of the withdrawal points 8 and upstream of the heating point 6, seen in the direction of water flow, as illustrated in the drawings. Such last position for measuring the concentration of monochloramine would provide a guaranteed minimum concentration value for all withdrawal points 8, not altered by thermal effect of heating, and useful for statistical and insurance purposes.

The monochloramine detection means 30 may be selected from the group of:
  redox sensors (ORP=oxidation reduction potential),
  amperometric probes to detect the concentration of total chlorine,
  colorimetric probes to detect the concentration of total chlorine,
  amperometric probes to detect the concentration of free chlorine (or excess chlorine),
  colorimetric probes to detect the concentration of free chlorine (or excess chlorine).

The ammonium detection means 17 may be selected from the group of:
  amperometric probes to detect the concentration of ammonium ions,
  colorimetric probes to detect the concentration of ammonium ions.

Figure 8:
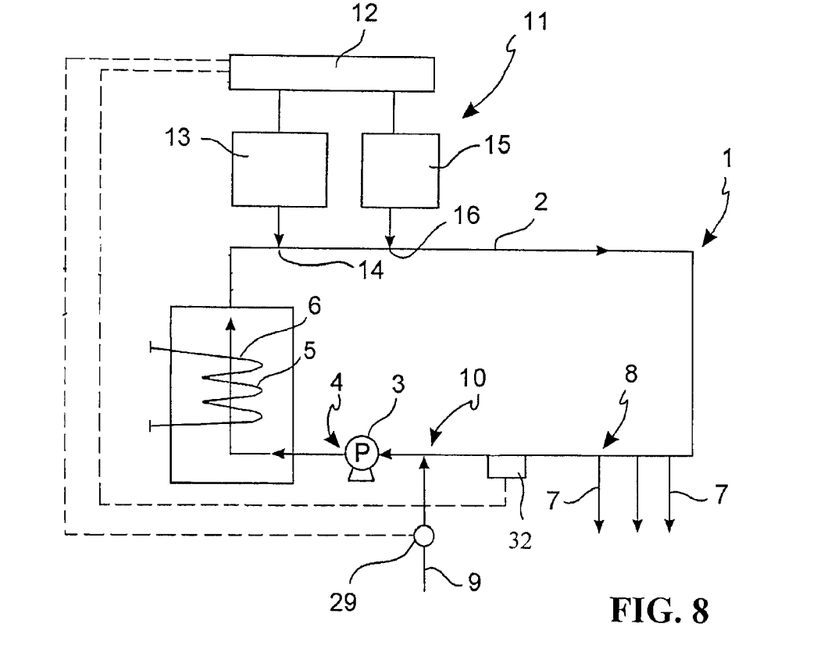
FIG. 8 shows the embodiment of FIG. 1, in which the monochloramine detector and the ammonium detector are made in a single sensor.

In a further embodiment, shown in FIG. 8, the monochloramine detection means and the ammonium detection means may be made in a single sensor 32 suitable to provide both the ammonium concentration signal and the monochloramine concentration signal to the control system 12.

The heating means 5 can keep the water temperature at values above 30° C., preferably between 35° C. and 65° C.

The concentration of monochloramine in the water is kept in the range between 0.1 mg/l and 10 mg/l, preferably between 1 mg/l and 3 mg/l which corresponds to a concentration of 1 ppm . . . 3 ppm.

In order to obtain a satisfactory reaction yield, the pH of the water in which the synthesis of the monochloramine is performed and, preferably, the pH of the water in the recirculation system of warm water 1, should be kept in the range from 7 and 9, preferably between 7.4 and 8.4.

Besides the disinfection system 11 so far described, the invention also relates to the disinfection method implemented thereby.

Obviously, a person skilled in the art may make further modifications and variations to the system and method of disinfection according to the present invention so as to satisfy contingent and specific requirements, while remaining within the scope of protection of the invention as defined by the following claims.

What is claimed is:

1. A sanitary warm water system, comprising a warm water recirculation system with:
   a water annular duct,
   a pump connected with the annular duct in a pumping point to circulate water in the annular duct,
   heating means connected with the annular duct in a heating point and configured to heat the water during the passage thereof through the heating point,
   one or more withdrawing ducts connected with the annular duct at respective withdrawing points, and
   a supplying duct connected with the annular duct in a supplying point,
   wherein the sanitary water system further comprises a disinfection system having:
      an electronic control system,
      a monochloramine generator in signal connection with the control system and connected with the annular duct in a disinfectant insertion point, wherein the generator is configured to synthesize monochloramine and to add the synthesized monochloramine to the warm water in the disinfectant insertion point,
      an ammonium ion abatement device in signal connection with the control system and connected with the annular duct in an abatement point, wherein the abatement device is configured to add chlorine or hypochlorites to the water at the abatement point, the abatement point being apart from the disinfectant insertion point
      ammonium detecting means in signal connection with the control system and connected with the annular duct at an ammonium detecting point, the ammonium detecting means being configured to detect a quantity representative of the ammonium ion concentration in the warm water at the ammonium detecting point, and to transmit a corresponding ammonium concentration signal to the control system,
   wherein the control system:
      activates the monochloramine generator and controls the monochloramine synthesis and addition, and
      activates the ammonium ion abatement device and controls the chlorine or hypochlorite addition as a function of the ammonium concentration signals, independently from the monochloramine generator activation.

2. The sanitary warm water system according to claim 1, wherein the monochloramine generator synthesizes the monochloramine externally to the warm water of the recirculation system and supplies the previously synthesized monochloramine into the annular duct.

3. The sanitary warm water system according to claim 1, wherein the ammonium ion abatement device comprises a chlorine or hypochlorite container connected via a metering device and a dispensing duct to the abatement point of the annular duct.

4. The sanitary warm water system according to claim 1, wherein the disinfectant insertion and abatement points are both downstream of the heating point and upstream of the withdrawing points (8), as seen in the water circulation direction.

5. The sanitary warm water system according to claim 4, wherein the abatement point is upstream of the disinfectant insertion point, as seen in the water circulation direction.

6. The sanitary warm water system according to claim 1, wherein the monochloramine generator synthesizes monochloramine with a slight chlorine excess.

7. The sanitary warm water system according to claim 1, wherein the abatement point is downstream of the withdrawing points and upstream of the heating point, as seen in the water flow direction in the annular duct.

8. The sanitary warm water system according to claim 1, wherein the disinfection system comprises a flow detector in signal connection with the control system and connected with the supplying duct, said flow detector being configured to detect a quantity representative of the water volume supplied at the supplying point of the annular duct and to transmit a corresponding volume signal to the control system,
   wherein the control system is configured to actuate the monochloramine generator and to control the monochloramine synthesis and addition as a function of the volume signal.

9. The sanitary warm water system according to claim 8, wherein the disinfection system comprises monochloramine detecting means in signal connection with the control system and connected with the annular duct in a monochloramine detection point, the monochloramine detecting means being configured to detect a quantity representative of the monochloramine concentration in the water at the monochloramine detecting point and to transmit a corresponding monochloramine concentration signal to the control system,
   wherein the control system is configured to actuate the monochloramine generator and to control the monochloramine synthesis and addition as a function of the monochloramine concentration signal.

10. The sanitary warm water system according to claim 9, wherein the monochloramine detecting point is downstream of the withdrawing points and upstream of the heating point, as seen in the water flow direction.

11. The sanitary warm water system according to claim 9, wherein the monochloramine detecting means and the ammonium detecting means are embodied by a single sensor device, which provides both the ammonium concentration signal and the monochloramine concentration signal to the control system.

12. A method for the disinfection of a warm water recirculation system with:
   a water annular duct, a pump connected with the annular duct in a pumping point to circulate water in the annular duct, heating means connected with the annular duct in a heating point and configured to heat water during the passage thereof through the heating point, one or more withdrawing ducts connected with the annular duct at respective withdrawing points, a supplying duct connected with the annular duct in a supplying point, wherein said method comprises the steps of:
synthesizing monochloramine in a monochloramine generator externally to the warm water recirculation system and adding the previously synthesized monochloramine to the warm water at a disinfectant insertion point of the annular duct, adding chlorine or hypochlorites to the warm water at an abatement point of the annular duct, the abatement point of the annular duct being apart from the disinfectant insertion point of the annular duct, detecting an ammonium ion concentration in the warm water at an ammonium detecting point of the annular duct, metering the chlorine or hypochlorite addition at the abatement point as a function of the detected ammonium ion concentration and independently from the monochloramine generator activation.

\* \* \* \* \*